United States Patent
Wakita

(10) Patent No.: US 6,867,319 B2
(45) Date of Patent: Mar. 15, 2005

(54) PROCESS FOR PREPARATION OF THIOCYANATO-BEARING ORGANOALKOXYSILANES

(75) Inventor: Keiji Wakita, Chiba (JP)

(73) Assignee: Dow Corning Toray Silicone Company, Ltd. (JP)

( * ) Notice: Subject to any disclaimer, the term of this patent is extended or adjusted under 35 U.S.C. 154(b) by 0 days.

(21) Appl. No.: 10/487,639
(22) PCT Filed: Sep. 20, 2002
(86) PCT No.: PCT/JP02/09743
§ 371 (c)(1), (2), (4) Date: Feb. 24, 2004
(87) PCT Pub. No.: WO03/027126
PCT Pub. Date: Apr. 3, 2003

(65) Prior Publication Data
US 2004/0210075 A1 Oct. 21, 2004

(30) Foreign Application Priority Data
Sep. 21, 2001 (JP) ........................... 2001-288152

(51) Int. Cl.$^7$ ................................................. G07F 7/04
(52) U.S. Cl. ........................................ 556/429; 556/414
(58) Field of Search ........................................ 556/414

(56) References Cited

U.S. PATENT DOCUMENTS 6,005,129 A    12/1999  Droge et al. ................. 556/414

Primary Examiner—Samuel Barts
Assistant Examiner—Lansana Nyalley
(74) Attorney, Agent, or Firm—Robert L. McKellar

(57) ABSTRACT

A process for the preparation of (D) thiocyanato-bearing organoalkoxysilanes represented by the general formula (3) NCS—$R^1$—Si$(OR^2)_n R^3_{3-n}$ wherein $R^1$ is a divalent hydrocarbon group having 1 to 6 carbon atoms, $R^2$ and $R^3$ are monovalent hydrocarbon groups, and the subscript n has a value of from 0 to 3, in which (A) a thiocyanic acid salt represented by the general formula (1) MSCN, wherein M is an alkali metal and (B) a halogenated alkylalkoxysilane represented by the general formula (2) $XR^1Si(OR^2)_n R^3_{3-n}$ wherein X is a halogen atom, and $R^1$, $R^2$, $R^3$, and the subscript n are the same as above, are reacted in the presence of (C) a phase transfer catalyst.

12 Claims, No Drawings

PROCESS FOR PREPARATION OF THIOCYANATO-BEARING ORGANOALKOXYSILANES

The present invention relates to a production process for thiocyanato-bearing organoalkoxysilanes.

In the prior art, there existed methods for producing thiocyanato-bearing alkoxysilanes, which are represented by compounds such as thiocyanatoalkylalkoxysilanes. For instance, Japanese Published Unexamined Patent Application No. Hei 12-229989 (equivalent to U.S. Pat. No. 6,005, 129) proposed a process for producing thiocyanatopropyltriethoxysilane by reacting γ-chloropropyltriethoxysilane with sodium thiocyanate in ethanol under elevated pressure. However, this process had the procedural disadvantage that the ethanol had to be removed upon termination of the reaction by distillation or other means. In addition, because the reaction was a pressure reaction, it required special pressure reaction equipment, which was economically disadvantageous, etc.

The present inventors arrived at the present invention as a result of studies directed towards the elimination of the above-described problems. It is an object of the present invention to provide a process for producing thiocyanato-bearing alkoxysilanes in a high yield, with high productivity.

The present invention relates to a "process for the preparation of (D) thiocyanato-bearing organoalkoxysilanes represented by the general formula (3) NCS—$R^1$—$Si(OR^2)_n R^3_{3-n}$ (where $R^1$ is a divalent hydrocarbon group having 1 to 6 carbon atoms, $R^2$ and $R^3$ are monovalent hydrocarbon groups, and the subscript n is 0 to 3), in which (A) a thiocyanic acid salt represented by the general formula (1) MSCN (where M stands for an alkali metal) and (B) a halogenated alkylalkoxysilane represented by the general formula (2) $XR^1Si(OR^2)_n R^3_{3-n}$ (where X is a halogen atom, and $R^1$, $R^2$, $R^3$, and the subscript n are the same as above) are reacted in the presence of (C) a phase transfer catalyst.

To explain this further, the thiocyanic acid salt (A) represented by the general formula (1) MSCN (where M stands for an alkali metal) is one of the raw materials used in the reaction, with the alkali metal M in the formula above exemplified by lithium, sodium, potassium, and rubidium. Of them, sodium and potassium are preferable. Such thiocyanic salts are exemplified by sodium thiocyanate and potassium thiocyanate. If the hydrolyzability of component (B) is high, component (A) causes a decrease in yields; for this reason, it is best used when thoroughly dried. Well-known conventional methods utilizing heating under reduced pressure or methods, in which azeotropic dehydration is carried out by adding an organic solvent, etc. can be employed in the drying operation. If the hydrolyzability of component (B) is low, component (A) does not have to be dehydrated and can be used in the form of an aqueous solution. The amount of the present component is preferably in the range of from 0.1 mol to 2.0 mol, and even more preferably, in the range of from 0.5 mol to 1.5 mol.

The halogenated alkylalkoxysilane of (B), which is represented by the general formula (2) $XR^1Si(OR^2)_n R^3_{3-n}$ (where X is a halogen atom, $R^1$ is a divalent hydrocarbon group having 1 to 6 carbon atoms, $R^2$ and $R^3$ are monovalent hydrocarbon groups, and the subscript n is 0 to 3), is also one of the raw materials used in the reaction, with the X in the formula above representing halogen atoms exemplified by chlorine and bromine atoms. The divalent hydrocarbon groups of $R^1$ are exemplified by methylene, ethylene, propylene, butylene, isobutylene, and other alkylene groups. The monovalent hydrocarbon groups of $R^2$ and $R^3$ are exemplified by methyl, ethyl, propyl, isopropyl, and other alkyl groups; vinyl, allyl, and other alkenyl groups; and phenyl, tolyl, and other aryl groups. Such halogenated alkylsilanes are exemplified by γ-chloropropyltrimethoxysilane, γ-chloropropyltriethoxysilane, γ-chloropropylmethyldimethoxysilane, γ-chloropropylmethyidiethoxysilane, γ-chloropropyldimethylmethoxysilane, γ-chloropropyidimethylethoxysilane, δ-chlorobutyltrimethoxysilane, δ-chlorobutylmethyldimethoxysilane, δ-chlorobutyltriethoxysilane, γ-chloro-β-methylpropyltrimethoxysilane, γ-chloro-β-methylpropylmethyidimethoxysilane, γ-chloro-β-methylpropyltriethoxysilane, γ-bromopropyltrimethoxysilane, γ-bromopropylmethyidimethoxysilane, and γ-bromopropyltriethoxysilane.

The phase transfer catalyst of (C), which is used to promote the reaction between component (A) and component (B), is exemplified by tributylammonium bromide, trioctylmethylammonium chloride, and other quaternary ammonium salts; tributylphosphonium chloride and other quaternary phosphonium salts; triethylamine, and other tertiary amines; crown ethers; polyethylene glycols; 1,8-diazabicyclo[5.4.0]undeca-7-ene (DBU), 1,5-diazabicyclo[4.3.0]-nona-5-ene (DBN), and other cyclic amine compounds. The amount of the phase transfer catalyst is preferably in the range of from 0.0001 mol to 20 mol, more preferably, in the range of from 0.001 mol to 10 mol, and even more preferably, in the range of from 0.001 mol to 5 mol per 1 mol of component (B).

In the preparation process of the present invention, component (A) and component (B) are reacted in the presence of component (C), with the reaction temperature at such time being preferably between 30° C. and 180° C., and, even more preferably, between 100° C. and 160° C. The reaction time may differ depending on the type and amount of component (A), component (B), and component (C); however, it typically lasts from 30 minutes to 15 hours.

In the preparation process of the present invention, component (B) serves both as a reaction substrate and as a solvent, which eliminates the need for a special organic solvent. However, organic solvents that are inert to component (A), component (B), and component (C) may be used if necessary. Such organic solvents are exemplified by toluene, xylene, octane, and dimethylformamide.

In the preparation process of the present invention, upon termination of the reaction between component (A) and component (B), it is preferable to remove salts produced as by-products and contained in the reaction product using filtration, dissolution in water, or other means. In addition, if necessary, further purification can be carried out by means of distillation.

Following the preparation process of the present invention ensures that (D) thiocyanato-bearing organoalkoxysilanes represented by the general formula (3) NCS—$R^1$—$Si(OR^2)_n R^3_{3-n}$ (where $R^1$, $R^2$, $R^3$ and the subscript n are the same as above) will be obtained in a high yield. Such thiocyanato-bearing organoalkoxysilanes are exemplified by γ-thiocyanatopropyltrimethoxysilane, γ-thiocyanatopropyltriethoxysilane, γ-thiocyanatopropylmethyldimethoxysilane, γ-thiocyanatopropylmethyldiethoxysilane, γ-thiocyanatopropyldimethylmethoxysilane, γ-thiocyanatopropyldimethylethoxysilane, δ-thiocyanatobutyltrimethoxysilane,
δ-thiocyanatobutylmethyldimethoxysilane,
δ-thiocyanatobutyltriethoxysilane, γ-thiocyanato-β-methylpropyltrimethoxysilane, γ-thiocyanato-β-methylpropylmethyidimethoxysilane, and γ-thiocyanato-β-methylpropyltriethoxysilane.

The thiocyanato-bearing organoalkoxysilanes obtained in accordance with the preparation process of the present invention as described above can be useful without any further treatment in applications such as silane coupling agents; in addition, they can be suitably employed as starting materials in the synthesis of other sulfur-containing organoalkoxysilanes or sulfur-containing organopolysiloxanes.

APPLICATION EXAMPLES

Below, the present invention is explained in detail by referring to application examples.

Application Example 1

106.9 g (1.10 mol) potassium thiocyanate, 240.8 g (1.00 mol) γ-chloropropyltriethoxysilane, and 0.77 g (0.005 mol) 1,8-diazabicyclo[5.4.0]undeca-7-ene (DBU) as a catalyst were placed in a 500-mL four-neck flask equipped with a reflux condenser, a stirrer, and a temperature gauge and subjected to agitation for 6 hours at 150° C. Subsequently, reaction by-products were removed by filtering off the reaction product. 242.3 g (0.92 mol) of the target γ-thiocyanatopropyltriethoxysilane were isolated by distilling the filtrate under reduced pressure. The yield of the γ-thiocyanatopropyltriethoxysilane was 92%.

Comparative Example 1

The reaction was conducted in the same manner as in Application Example 1, except that the 1,8-diazabicyclo[5.4.0]undeca-7-ene (DBU) was not added to the 500-mL four-neck flask equipped with a reflux condenser, a stirrer, and a temperature gauge; the target thiocyanatopropyltriethoxysilane was not produced at all.

Application Example 2

106.9 g (1.10 mol) potassium thiocyanate, 198.7 g (1.0 mol) γ-chloropropyltrimethoxysilane, 0.77 g (0.005 mol) 1,8-diazabicyclo[5.4.0]undeca-7-ene (DBU) as a catalyst, and 30 g toluene were placed in a 500-mL four-neck flask equipped with a reflux condenser, a stirrer, and a temperature gauge and subjected to agitation for 10 hours at 125° C. Water was added to the resultant reaction product to induce phase separation, and reaction by-products were removed. 199.2 g (0.90 mol) of the target γ-thiocyanatopropyltrimethoxysilane were isolated by distilling the toluene layer under reduced pressure. The yield of the γ-thiocyanatopropyltrimethoxysilane was 90%.

Application Example 3

106.9 g (1.10 mol) potassium thiocyanate, 182.7 g (1.0 mol) γ-chloropropylmethyldimethoxysilane, and 1.61 g (0.005 mol) tetrabutylammonium bromide as a catalyst were placed in a 500-mL four-neck flask equipped with a reflux condenser, a stirrer, and a temperature gauge and subjected to agitation for 12 hours at 120° C. Subsequently, reaction by-products were removed by filtering off the reaction product. 180.7 g (0.88 mol) of the target γ-thiocyanatopropylmethyldimethoxysilane were isolated by distilling the filtrate under reduced pressure. The yield of the γ-thiocyanatopropylmethyldimethoxysilane was 88%.

In the preparation process of the present invention, component (A) and component (B) are reacted in the presence of component (C), and, for this reason, thiocyanato-bearing organoalkoxysilanes can be produced in a high yield, with high productivity.

What is claimed is:

1. A process for the preparation of (D) thiocyanato-bearing organoalkoxysilanes represented by the general formula (3) NCS—$R^1$—$Si(OR^2)_n R^3_{3-n}$ wherein $R^1$ is a divalent hydrocarbon group having 1 to 6 carbon atoms, $R^2$ and $R^3$ are monovalent hydrocarbon groups, and the subscript n has a value of from 0 to 3, in which (A) a thiocyanic acid salt represented by the general formula (1) MSCN wherein M is an alkali metal and (B) a halogenated alkylalkoxysilane represented by the general formula (2) $XR^1Si(OR^2)_n R^3_{3-n}$ wherein X is a halogen atom, and $R^1$, $R^2$, $R^3$, and the subscript n are the same as above, are reacted in the presence of (C) a phase transfer catalyst.

2. The preparation process according to claim 1, in which M of the general formula (1) is selected from the group consisting of sodium and potassium.

3. The preparation process according to claim 1, in which component (A) is potassium thiocyanate.

4. The preparation process according to claim 1, in which component (B) is γ-chloropropyltrimethoxysilane.

5. The preparation process according to claim 1, in which component (B) is γ-chloropropyltriethoxysilane.

6. The preparation process according to claim 1, in which component (B) is γ-chloropropylmethyldimethoxysilane.

7. The preparation process according to claim 1, in which component (C) is 1,8-diazabicyclo{5.4.0}undeca-7-ene.

8. The preparation process according to claim 1, in which component (C) is tetrabutylammonium bromide.

9. The preparation process according to claim 1, in which the thiocyanato-bearing alkoxysilane is γ-thiocyanatopropyltrimethoxysilane.

10. The preparation process according to claim 1, in which the thiocyanato-bearing alkoxysilane is γ-thiocyanatopropyltriethoxysilane.

11. The preparation process according to claim 1, in which the thiocyanato-bearing alkoxysilane is γ-thiocyanatopropylmethyldimethoxysilane.

12. The preparation process according to claim 1, in which the thiocyanato-bearing alkoxysilane is γ-thiocyanatopropylmethyldiethoxysilane.

* * * * *